United States Patent [19]

McRae

[11] Patent Number: Plant 6,522

[45] Date of Patent: Jan. 10, 1989

[54] LILY NAMED IRISH PIXIE

[75] Inventor: Edward A. McRae, Boring, Oreg.

[73] Assignee: Melridge, Inc., Aurora, Oreg.

[21] Appl. No.: 6,025

[22] Filed: Jan. 22, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of hybrid lily plant bearing large clusters of flowers of excellent form and of medium to large size particularly characterized by their rich orange coloration accented by a golden orange midrib, the flowers being borne in a single compact raceme comprising five to eight buds carried on a single erect stem having an average height of about two to two and one-half feet. The short stature of this plant, together with its short but full leaves taken together with its large flowers, make it especially suitable as a pot plant variety. The color pattern and silhouette of this new lily plant are entirely new in the upright Asiatic divisions of lilies suited to forcing and to mass commercial cultivation.

This plant is highly resistant to disease and shows high tolerance of virus, making it an excellent garden plant, and the bulbs may be precooled and forced throughout the year for pot plant production. The clone of this new variety is vigorous and is a good grower and propagator.

1 Drawing Sheet

BACKGROUND OF THE NEW PLANT

My new variety of lily plant originated as a seedling selected from a group of seedlings planted by me at Sandy, Ore., and resulting from my crossing of the clonal cultivar 'Charisma' as the seed parent with the clonal cultivar 'Sunray' as the pollen parent; this crossing having been done with the object of producing lilies in shades of orange and yellow well suited to forcing for pot plant production out of season, a result heretofore unknown in the lily breeding art.

This selected seedling was asexually reproduced by me at Sandy, Ore., by bulb scale propagation and by natural propagation from bulblets with such satisfactory results that propagation in this manner was continued by me and under my direction through several successive generations, which demonstrated that the novel characteristics of this new plant would remain true from generation to generation and appeared to be firmly fixed.

By observation of this new plant through successive generations, I have found that the variety remains short and is not overly susceptible to bud abortion when forced into flower out of season as a pot plant and in addition, I have found that the clone possesses to a high degree the desirable characteristics of hybrid vigor, great hardiness, and disease resistance, possessing all of the desired characteristics of form, color, and habit.

I have found that the new plant is well suited to forcing out of season when the bulbs are dug at the appropriate time and properly precooled; October-dug bulbs, properly precooled and potted in January, will flower under glass in western Oregon in an average of sixty-five to seventy-five days, with no supplementary lighting and at moderate greenhouse temperature.

DESCRIPTION OF THE DRAWING

My new lily variety is illustrated in the accompanying photographic drawing, which shows fully opened blooms in full color illustrating the flower form and the tepal arrangement, the novel and distinctive rich orange tepal coloration with the golden orange midribs, all of which is accented by a small ring of spots encircling the center of the flower.

DESCRIPTION OF THE NEW VARIETY

The following is a detailed description of my new variety of Asiatic hybrid lily, with nomenclature according to The International Lily Register (The Royal Horticultural Society of London, England, Second Edition, 1969), and with the color designations according to the R.H.S. Colour Chart published by The Royal Horticultural Society in 1966.

THE PLANT

Origin: Seedling.

Parentage:

*Seed parent.*—Lilium 'Charisma' U.S. Plant Pat. No. 4,180.

*Pollen parent.*—Lilium 'Sunray' (unpatented).

Classification:

*Horticultural.*—Upright Asiatic Hybrid Lily, Division I-A, according to the Horticultural Classification of Lilies by The Royal Horticultural Society of London, England.

*Commercial.*—Hybrid Lilium Clone.

Form: Single, erect and stately.

Height: About 40 to 60 cm. for stems produced by glasshouse forcing of bulbs of about 15 to 18 cm. in circumference, provided that the light levels are adequate. Low light levels may cause "stretching".

Growth: Vigorous and upright.

Foliage:

*Quantity.*—Abundant.

*Size of leaf.*—About 5 to 8 cm. long and about 1 cm. wide.

*Shape of leaf.*—Lanceolate with acuminate tip.

*Texture.*—Leathery.

*Aspect.*—Glossy; lightly pubescent along the margins.

*Color.*—Dark green, lighter on the under side.

Bulbs:

*Size.*—Various, depending upon age and ranging to about 25 cm. in circumference as commercially used.

*Color.*—White.

THE BUD

Form: Long ovoid and obtuse at base and tip.

Size: About 8 to 9 cm. long and about 5 cm. in circumference just prior to opening.

Opening rate: The bud opens slowly, taking about one hour in response to morning light.

Color: Buff orange, just prior to opening and as the tepals begin to unfurl and being lightly pubescent.

Peduncle:

*Length.*—Averages about 4 to 5 cm. It may elongate, however, if the light levels are too low or if the bulbs have been improperly stored prior to forcing.

*Color.*—Deep green with soft plum overlay.

THE FLOWER

Blooming habit: Annually, flowering once and profusely in midseason.

Size:

*Average diameter.*—About 13 to 15 cm.

Borne: As a single compact raceme on an upright stem and producing about 5 to 8 buds from a bulb of about 12 to 15 cm. in circumference.

Shape: Cup-shaped upon first opening and becoming somewhat flattened as the tepals recurve during the second day.

Tepalage:

*Number.*—Typical of genus Lilium with six imbricated tepals in hexagonal arrangement.

*Size of tepals.*—Outer tepals average about 3 cm. wide. The inner tepals average about 4 to 4.5 cm. wide.

*Color.*—The flowers of this variety are distinguished by their unusual color pattern. The base or primary color is a rich orange, 28A, and there is a longitudinal band of golden orange, 26A-B, about 1 cm. wide extending for about 2 cm. along the midrib of each tepal outwardly from the nectaries. There is a light flush of deeper orange, 30B, along the tepal margins and at their tips. Under certain conditions of light and temperature, the base of this golden orange band may be lightly brushed with a soft purple-red marking, 47C, about 5 mm. long and about 2 to 4 mm. wide. The border of the nectary furrow is lightly pubescent and white.

*Spotting.*—The basal third of each tepal is marked with small magenta-purple spots just above the nectaries and the summation of the spots on all the tepals provides a ring of spots encircling the center of the flower.

*Tepal longevity.*—The tepals stay on the stems about three weeks.

Pedicel:

*Length.*—Averages about 5 to 10 cm.

*Form.*—Sturdy and ascending up to about 60 degrees from the horizontal and very rarely having secondary buds.

*Color.*—Dark green with a light plum overlay.

Color changes: The flower color deepens to 30B-C as the flower ages, if the light levels are adequate for cut flower and pot plant maintenance.

Aspect: The flower is shiny.

Disease resistance: The flower and plant are resistant to disease; in particular, they are resistant to Fusarium bulb rot and Botrytis blight.

Lasting quality: The flower is long lasting, both on the plant and as a cut flower.

REPRODUCTIVE ORGANS

Stamens: Six in number and in arrangement typical of genus Lilium.

*Anthers (dehisced) and pollen.*—Color — Greyed orange, 172A.

*Filaments.*—About 5 cm. long.

Pistil:

*Number.*—One.

*Length.*—About 5 cm.

*Stigma.*—Color: Soft orange with deep plum overlay.

Ovary: The ovary is characteristic of the genus Lilium.

THE FRUIT

Fertility: The fruit is fertile.

Shape: Ovoid.

Color at maturity: Soft brown, sometimes overlaid with soft plum.

This new variety most closely resembles 'Charisma' but it has spotted flowers, a much higher bud count, and shorter leaves. It is also more reliable than 'Charisma' and more uniform in its forcing performance. It resembles its sister clone 'Summer Pixie' but it differs from it in its slightly lighter orange coloration with a more orange and less gold tone of its midrib stripe, which is less conspicuous than that of 'Summer Pixie'. The new variety differs from 'Summer Pixie' by its much lighter colored stems and its only slightly pubescent stems and leaves.

I claim:

1. A new and distinctive variety of Asiatic hybrid lily plant, substantially as herein shown and described, particularly characterized by its rich orange flowers accented by lighter colored orange midribs and a decorative central ring of spots; the excellence of its flower form; and by its short stemmed, short leaved, upright flowering silhouette; and its versatility both as a garden plant and as a pot plant variety.

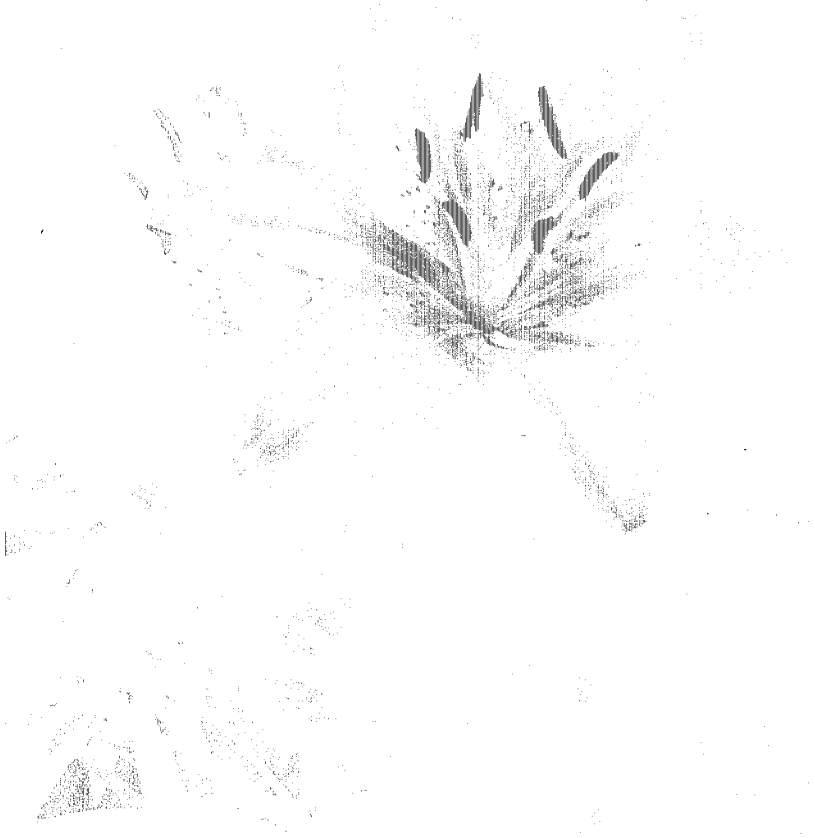

* * * * *